United States Patent [19]

Gong

[11] 4,368,268
[45] Jan. 11, 1983

[54] DIRECT FERMENTATION OF D-XYLOSE TO ETHANOL BY A XYLOSE-FERMENTING YEAST MUTANT

[75] Inventor: Cheng-Shung Gong, West Lafayette, Ind.

[73] Assignee: Purdue Research Foundation, West Lafayette, Ind.

[21] Appl. No.: 263,925

[22] Filed: May 15, 1981

[51] Int. Cl.$^3$ ............................................... C12D 7/06
[52] U.S. Cl. .................................... 435/161; 435/163; 435/921
[58] Field of Search ......................... 426/161, 163–165, 426/921, 924, 930, 940, 944

[56] References Cited

U.S. PATENT DOCUMENTS

| | | | |
|---|---|---|---|
| 1,857,429 | 5/1932 | Christensen | 435/163 X |
| 2,481,263 | 9/1949 | Tsuchiya et al. | 435/161 X |
| 4,288,550 | 9/1981 | Ishida et al. | 435/940 X |

OTHER PUBLICATIONS

Gong, C. S. et al., "Production of Ethanol from D-xylose by Using D-xylose Isomerase and Yeasts", Applied and Environmental Microbiology, Feb. 1981, pp. 430–436.

Primary Examiner—Robert A. Yoncoskie
Attorney, Agent, or Firm—Cushman, Darby & Cushman

[57] ABSTRACT

A process for obtaining ethanol directly from D-xylose through fermentation of D-xylose by xylose-fermenting yeast mutants. The process provides for obtaining ethanol from hemicellulose hydrolyzates through yeast fermentation of D-xylose to ethanol. Furthermore, the process also provides for obtaining ethanol from a mixture of cellulose and hemicellulose hydrolyzates through yeast fermentation of D-glucose and D-xylose directly and simultaneously to ethanol.

18 Claims, 4 Drawing Figures

DIRECT FERMENTATION OF D-XYLOSE TO ETHANOL BY A XYLOSE-FERMENTING YEAST MUTANT

BACKGROUND OF THE INVENTION

D-xylose, a five-carbon sugar, is a naturally occurring carbohydrate present in large quantities in a wide variety of plant materials. It often comprises over 60% of the recoverable sugars derived from hemicelluloses.

Numerous microorganisms such as bacteria and mycelial fungi are known to produce small amounts of ethanol and other products from D-xylose under fermentation conditions. These methods however, do not provide a means for the conversion of D-xylose to ethanol in high yields.

Many yeasts are capable of fermenting hexoses to ethanol anaerobically in high yields. However, no yeasts have been reported to ferment pentoses (or specifically D-xylose) to ethanol effectively, even though many yeasts are capable of both metabolizing pentoses aerobically, and in many cases, producing polyols (e.g., xylitol, and arabitol) as the metabolic by-products. Therefore, D-xylose, which is derived primarily from hemicellulosic materials, has been regarded as a nonfermentable sugar.

Several bacteria (e.g., clostridia) and mycelial fungi (e.g., Mucor spp., Rhizopus spp., Monilia spp., and Fusaria) are known to metabolize as well as ferment D-xylose to ethanol. However, for ethanol production from biomass, yeasts are preferred over bacteria and mycelial fungi. The yeast process for fermenting glucose to ethanol is a relatively simple and well-studied process. On the other hand, bacterial fermentation of D-xylose has not been satisfactory due to the low yield and the undesirable generation of organic acids [e.g., lactic acid] as fermentation products along with ethanol, as confirmed in U.S. Pat. No. 1,857,429. Mycelial fungal fermentation of D-xylose has not been satisfactory either, due to the slow-rate of fermentation and low-yield of ethanol.

The biological conversion of five-carbon sugars derived from hemicellulose to ethanol is important in order to fully utilize biomass so as to produce liquid fuels, especially in view of the fact that vast quantities of hemicellulosic materials are readily available. Unfortunately these materials have been greatly under-utilized due to the lack of the ability of proper organisms to convert D-xylose to ethanol efficiently.

Accordingly, it is the primary object of the present invention to provide a new process for the production of ethanol from D-xylose using novel xylose-fermenting yeast mutants.

It is a further object of the present invention to provide a means for production of ethanol from both D-xylose and other six-carbon sugars, simultaneously. These and other objects will be more apparent from the discussion below.

SUMMARY OF THE INVENTION

The present invention provides a process for producing ethanol from either D-xylose or D-xylose containing hemicellulose hydrolyzates or plant material hydrolyzates by fermentation which comprises inoculating D-xylose-fermenting yeast mutants capable of producing ethanol from D-xylose in over 80% yield. Moreover, the present invention also relates to inoculating same yeast mutants capable of producing ethanol from glucose containing hydrolyzates and also from D-xylose containing hydrolyzates by fermenting both glucose and xylose, simultaneously. The product ethanol and yeast cells are then separated. The following discussion demonstrates the process of this invention wherein D-xylose and plant hydrolyzates are used as the starting fermentation substrates.

I. Production of Ethanol from D-xylose

As one embodiment of the present invention, there is provided a process for producing ethanol in a yield of over 80% of theoretical value by aerobic or anaerobic fermentation of D-xylose by xylose fermenting yeast mutants. In carrying out such a process according to the present invention, yeast mutants that are created through either mutation mutagens (e.g., chemical or physical) may be employed. Also included within the scope of the "mutants" of the present invention are those obtained by protoplast fusions or recombinant DNA techniques. These mutation mutagens and the like are obtained from a parent strains which have a limited ability in their unmutated state to ferment D-xylose to ethanol. For example *Candida diddensii, Candida utilis, Candida tropicalis, Candida subtropicalis, Pachysolen tannophilus, Saccharomyces diastaticus, Saccharomycopsis fibuligera* and *Torula candida* and other D-xylose utilizing yeasts may be used as parent strains for the isolation of mutants through chemical, physical biological mutation. Hybrid formation and DNA recombination techniques may also be employed.

A preferred method for obtaining the desired mutant strain involves initially isolating (randomly) a single colony of the parent strain which is then subjected to ultra-violet (uv) radiation to induce mutation. Thereafter, the resultant mutant strain is screened to isolate the specific colony or colonies having the best capability to utilize the D-xylose to produce ethanol.

In producing ethanol from D-xylose, yeast mutants are inoculated into the medium containing appropriate growth nutrients (e.g., yeast extracts, malt extracts and peptone) and D-xylose as carbon and fermentation substrates. The D-xylose concentration can be varied in a wide range, 1 to 40%, preferably 5 to 30%. The fermentation is conducted under aerobic or anaerobic conditions while maintaining the incubation at a temperature range of about 22° to 40° C., and preferably at about 30° C. After about 10 hours to 4 days (depending on sugar concentration, yeast density and other fermentation conditions), the D-xylose is consumed, and the ethanol so produced is accumulated.

II. Production of Ethanol from Sugarcane Bagasse Hemicellulose Hydrolyzate

The hemicellulose hydrolyzate from sugarcane bagasse which contains 6.4% D-xylose, 1.8% L-arabinose, and 0.6% D-glucose was used as fermentation substrate. Hemicellulose hydrolyzate was obtained by acid hydrolysis of bagasse. The pH was then adjusted to about 6 with the removal of undesired precipitants. To this hydrolyzate, D-xylose fermenting yeast mutant was inoculated ($2 \times 10^6$ cell/ml) and fermentation was carried out at 30° C. for 24 hrs. As a result, ethanol was produced in a high yield from D-xylose. The adjustment of pH mentioned is conducted by using calcium oxide and/or caustic soda. The pH range may vary from about 4 to about 8, and preferably is about 6. For further production of ethanol from additional hydrolyzates, the yeasts can be recycled and reused.

III. Production of Ethanol from Cellulose and Hemicellulose Hydrolyzate of Vegetative Materials The cellulose and hemicellulose hydrolyzates which contain higher amounts of D-glucose and D-xylose were also used as a fermentation substrate (i.e., 6.8% D-glucose, 5.3%, D-xylose, and 0.8% L-arabinose). Fermentation was carried out as described above. As a result, ethanol was produced in the desired high yields.

Figure 1:
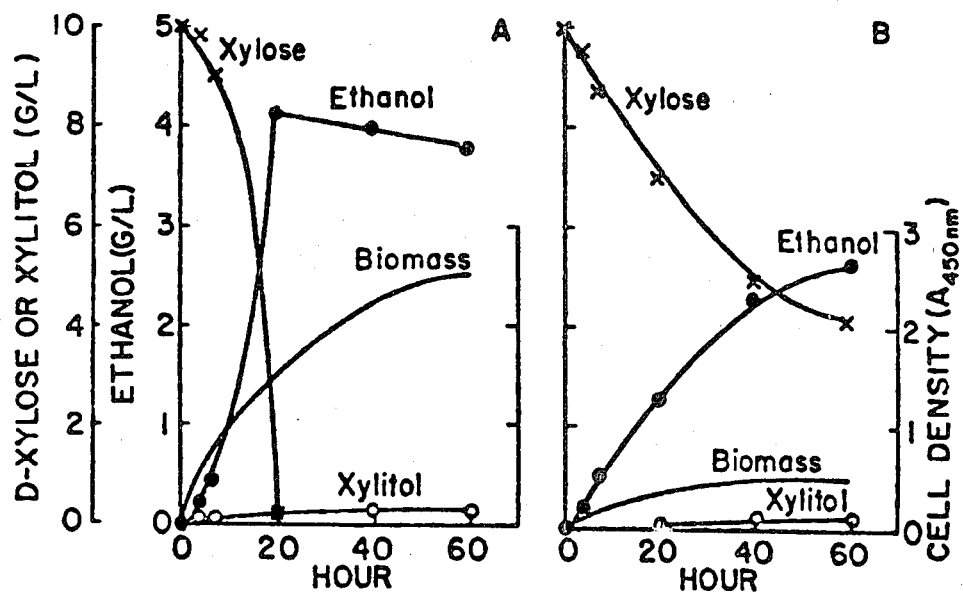
FIGS. 1 and 2 are graphs depicting cell growth and ethanol production from D-xylose (1% in FIG. 1 and 5% w/v in FIG. 2) by Candida sp. XF 217, graphs A representing aerobic conditions and graph B anaerobic conditions.

The following examples are offered in order to more fully describe the present invention, but are not to be construed as limiting the scope thereof as departures may be made therefrom.

EXAMPLE 1

(Comparative)

Several existing yeast strains were examined for their ability to ferment D-xylose to ethanol. Those organisms so capable were inoculated into the culture liquid medium containing 0.3% Bacto-yeast extract, 0.3% Difco Malt-extract and 0.5% Bacto-peptone (referred to herein as YM medium) with 1% D-xylose and incubated with shaking at 30° C. for 24 hours. After incubation additional xylose was added (5%, wt/v) and the fermentation was carried out either at non-aerated or shaking conditions for 48 hrs at 30° C. The results of xylose fermentation is shown in Table 1 below. It indicated that most organisms tested utilized D-xylose aerobically and some produce xylitol as fermentation product, but none are able to produce high levels of ethanol. Under non-aerated condition, some yeasts utilized xylose again with xylitol as fermentation product but only trace amounts of ethanol was produced. The results indicate that none of the yeast tested could effectively ferment xylose to ethanol. Earlier, Barnett (Barnett, J. A., Adv. Carbohydrate Chem. Biochem. 32: 125–234, 1976) surveyed 434 species of yeast, about half of the species were found to assimilate D-xylose aerobically and none are able to ferment D-xylose anaerobically to produce ethanol. This together with the results noted in Table 1 confirm that yeasts are not able to effectively ferment (i.e., yields greater than 50% ) D-xylose to ethanol.

TABLE 1

| Fermentation of D-Xylose by Yeasts | | | |
|---|---|---|---|
| Yeast | ATCC No. | Percent (%, w/v) Ethanol Produced | Xylitol |
| Candida diddensii | 20213 | 0.12 | 0.22 |
| Candida utilis | 9256 | 0.38 | 0.31 |
| Candida tropicalis | 1369 | 0.19 | 0.62 |

TABLE 1-continued

| Fermentation of D-Xylose by Yeasts | | | |
|---|---|---|---|
| Yeast | ATCC No. | Percent (%, w/v) Ethanol Produced | Xylitol |
| Saccharomyces cerevisiae | 24860 | 0 | 0.17 |
| Saccharomyces diastaticus | 28338 | 0.14 | 0.25 |
| Saccharomyces rouxii | 32901 | 0 | 0.35 |
| Saccharomyces saki | 26421 | 0 | 0.2 |
| Schizosaccharomyces pombe | 26192 | 0 | 0 |
| Hansenula polymorpha | 14754 | 0 | 0.2 |
| Pachysolen tannophilus | 32691 | 0.32 | 0.52 |
| Saccharomycopsis fibuligera | 32693 | 0.12 | 0.33 |
| Torula candida | 20214 | 0.12 | 0.17 |

Fermentation was carried out at 30° C. under fermentation conditions with shaking at 200 rpm.

The initial cell density was $2 \times 10^8$ cells per ml.

The initial sugar concentration was 5% (w/v) and incubation was for 48 hr.

EXAMPLE 2

Yeast mutant strains isolated from Candida sp. XF 217 (ATCC No. 20615) were examined for their ability to ferment D-xylose to ethanol aerobically or anaerobically. Organisms were inoculated into the liquid medium (YM medium) with 1% xylose and incubated with shaking at 30° C. for 24 hours. After initial incubation, an additional 5% xylose was added to the fermentation medium and the fermentation was carried out for 24 hours. At the end of the fermentation period, this broth was then centrifuged to remove yeast cells. The ethanol produced was then analyzed and quantified by gas chromatography. As shown in Table 2 below, the mutant strains ferment xylose to ethanol while the parent strain is unable to produce ethanol from xylose in high yields.

TABLE 2

| | ETHANOL[a] PRODUCTION OF CANDIDA SP. AND XF 217[b] | | | |
|---|---|---|---|---|
| | Candida sp. | | XF 217 | |
| Sugars[c] | Aerobic | Anaerobic | Aerobic | Anaerobic |
| Glucose | 10.96 | 17.85 | 11.47 | 18.71 |
| Fructose | 11.33 | 17.02 | 13.71 | 17.55 |
| Xylose[d] | 2.27(42) | 1.52(17.3) | 11.63(6.1) | 3.10(2.9) |
| L-Arabinose | 0.06 | 0.16 | 0.12 | 0.68 |
| Xylitol | 0.02 | 0.08 | 0.05 | 0.17 |
| Sucrose | 15.15 | 20.64 | 15.14 | 22.66 |
| Maltose | 10.58 | 14.53 | 6.87 | 9.44 |
| Lactose | 0.02 | 0.12 | 0.06 | 0.03 |

[a]Ethanol concentration was expressed as grams per liter.
[b]Incubation was carried out in flask cultures at 30° C., shaken at 200 rpm. The initial pH was 5.6, and the initial cell density was $1 \times 10^7$ cells per ml.
[c]The initial sugar concentration was 5% (w/v), and cultures were incubated for 24 hr.
[d]Numbers in parentheses indicate grams/liter xylitol produced.

Both Candida sp. and mutant strain XF 217 utilize D-glucose, D-fructose, D-xylose, L-arabinose, xylitol, sucrose and maltose as carbon and energy sources. When the yeasts from exponential growth phase were incubated with sugars under either growing (aerobic) or fermentative (anaerobic) conditions, ethanol was produced when the added sugars were D-glucose, D-fructose, sucrose or maltose. When D-xylose was the sugar used, Candida sp. produced xylitol, but XF 217 produced ethanol (Table 2). These results further indicate that mutant strain XF 217 produces ethanol preferentially over xylitol production. In addition, the fermentation of D-xylose by XF 217 differs from the fermentation of hexose substrates, since oxygen must be available for enhanced ethanol production from D-xylose in XF 217.

Figure 2:
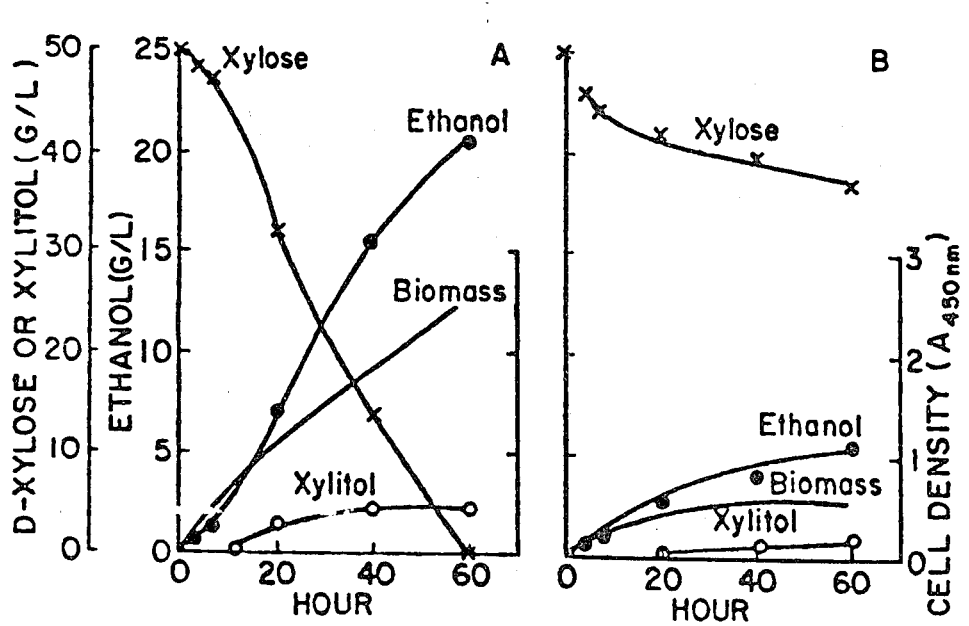

FIGS. 1 and 2 depict the growth and ethanol production by XF 217 when grown in 1% and 5% D-xylose as the sole energy and carbon source under aerated and fermentative conditions. The rates of growth and ethanol production are slower under fermentative conditions. These results indicate that oxygen is required for growth as well as the production of ethanol. Similar results were observed when higher concentration of D-xylose (5% w/v) (FIG. 2) was used as substrate. Under these conditions, the ethanol yield was between 80% and 85% of the theoretical value.

EXAMPLE 3

Figure 3:
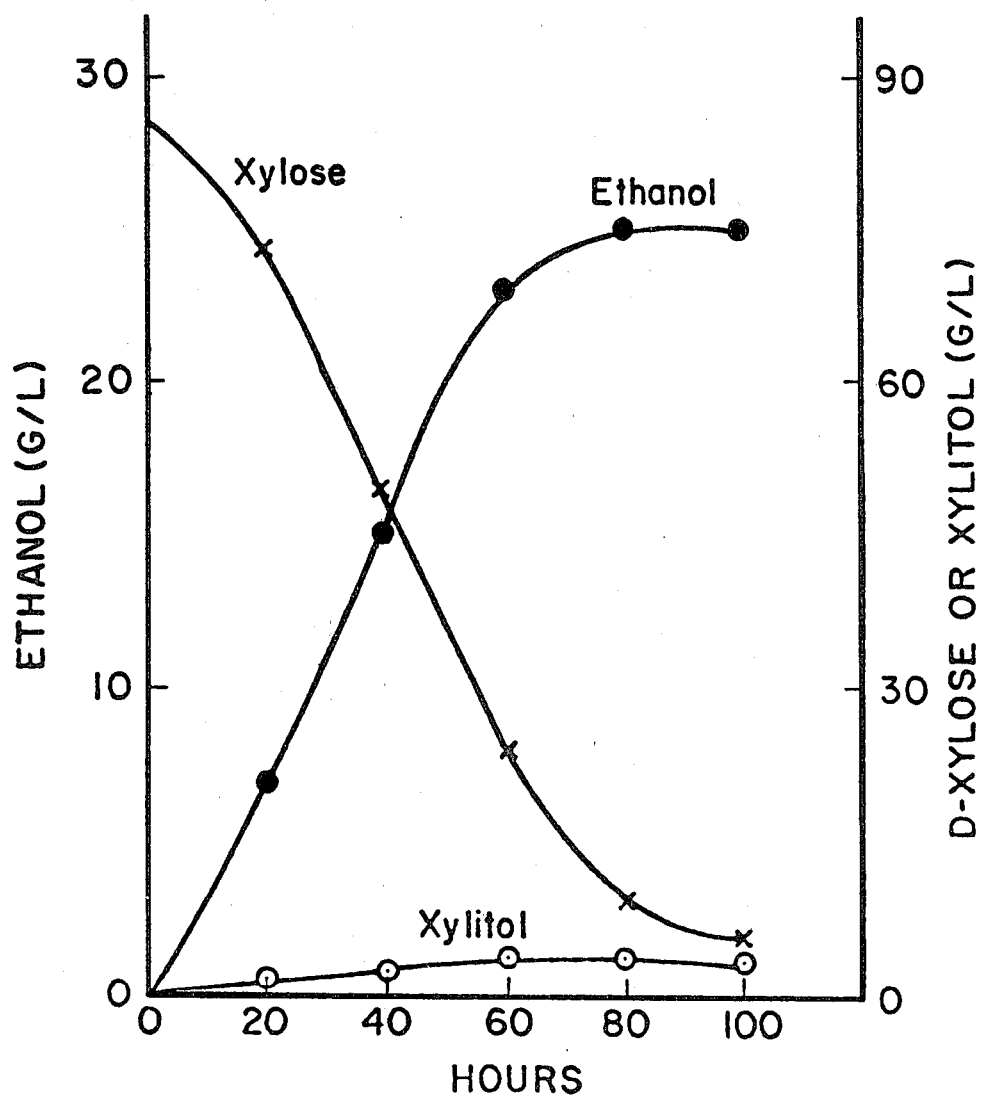
FIG. 3 is a graphic depiction of the ethanol production from the aerobic fermentation of hemicellulose hydrolyzate by XF 217.
Figure 4:
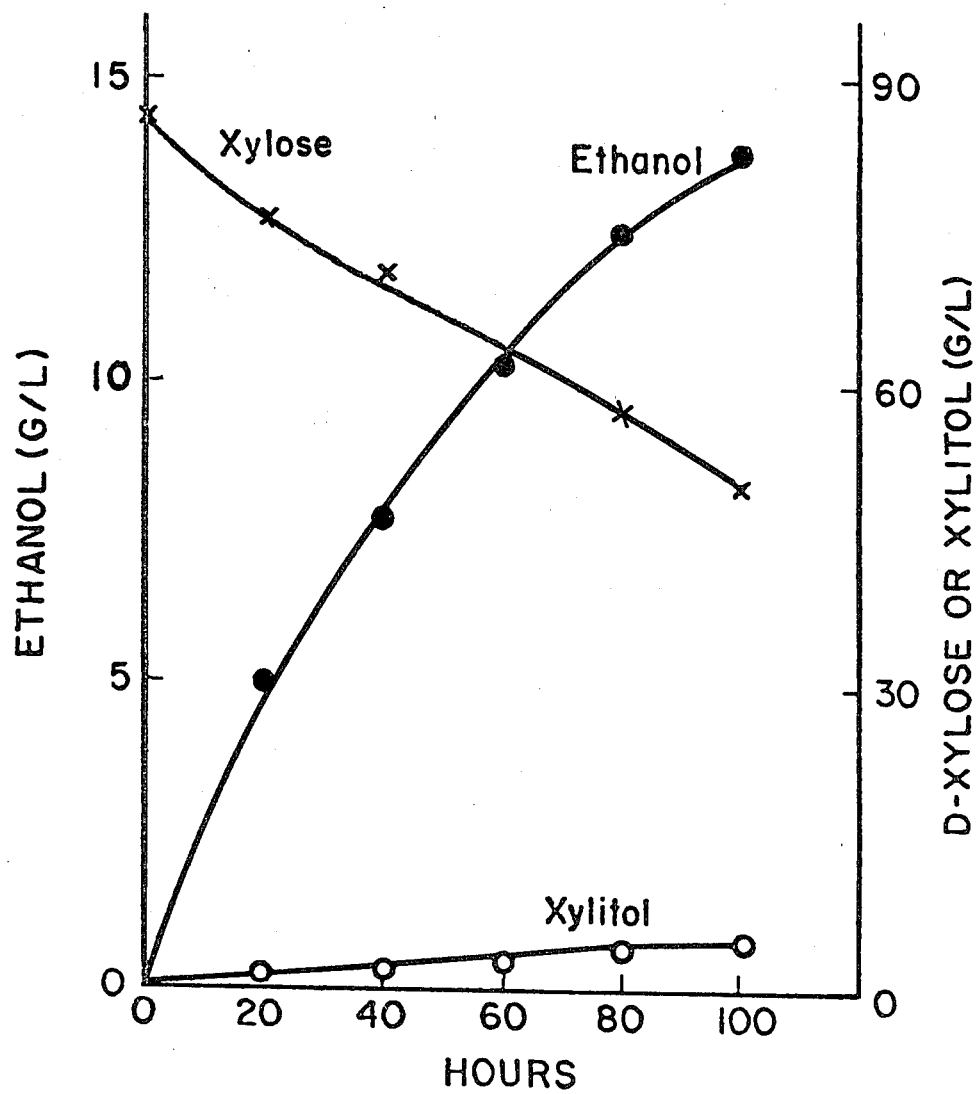
FIG. 4 represents the ethanol produced from the anaerobic fermentation of hemicellulose hydrolyzate by XF 217.

Mutant strain of Candida sp. XF 217 (ATCC No. 20615) was inoculated into a liquid medium containing hemicellulose hydrolyzate and incubated (in two separate preparations) both under aerobic conditions with shaking at 30° C. as well as under anaerobic conditions at 30° C. Samples were taken over a period of time (see FIGS. 3 and 4) and centrifuged to remove yeast cells. D-xylose concentration was measured by liquid chromatography, and the ethanol produced was measured by gas chromatography. Yeast cell growth was monitored by optical density at 450 nm and expressed as relative growth. The results shown in FIGS. 3 and 4 indicate that the XF 217 yeast is able to convert D-xylose contained in hemicellulose hydrolyzate to ethanol aerobically as well as anerobically.

The use of a single organism such as yeast to convert both hexose and pentose to ethanol in high yields would be ideal. The present invention demonstrates that the D-xylose fermenting yeast strains such as XF 217 can be used to achieve this goal.

The invention having been thus described, it will be appreciated that various departures can be made therefrom without departing from the scope thereof. Furthermore, the invention may comprise, consist, and/or consist essentially of the hereinbefore recited materials and steps.

What is claimed is:

1. A process for the direct fermentation of D-xylose to ethanol which comprises inoculating a medium comprising growth nutrients and D-xylose with a yeast mutant of the strain Candida sp. having an ability to ferment D-xylose to ethanol with a bioconversion yield of at least 80%, permitting the inoculated medium to ferment for a period of time sufficient to achieve a conversion of D-xylose to ethanol of at least 80% and recovering the ethanol so produced as product.

2. A process according to claim 1 wherein the yeast mutant is Candida sp. XF-217.

3. A process according to claim 1 wherein the initial concentration of D-xylose in said medium ranges from 1 to about 40 percent on a weight/volume basis.

4. A process according to claim 3 wherein said initial concentration ranges from about 5 to 30 percent.

5. A process according to claim 1 wherein fermentation is carried out at a temperature ranging from about 22° to about 40° C.

6. A process according to claim 5 wherein said temperature is about 30° C.

7. A process according to claim 1 wherein fermentation is carried out at a pH ranging from about 4 to about 8.

8. A process according to claim 7 wherein said pH is about 6.

9. A process according to claim 1 wherein fermentation is carried out under aerobic conditions.

10. A process according to claim 1 wherein fermentation is carried out under anaerobic conditions.

11. A process according to claim 1 wherein the D-xylose is contained in hemicellulose hydrolyzate.

12. A process according to claim 1 wherein said medium also contains cellulose hydrolyzate material.

13. A process for the direct fermentation of D-xylose to ethanol which comprises inoculating a medium comprising growth nutrients and D-xylose in an amount of from 1 to about 40% by weight/volume of said medium with a yeast mutant of the strain Candida sp. having an ability to ferment D-xylose to ethanol with a bioconversion yield of at least 80%, fermenting the innoculated medium at a temperature ranging from about 22° to about 40° C. and a pH ranging from about 4 to about 8 for a period of time sufficient to achieve at least an 80% conversion of the D-xylose to ethanol, and recovering the ethanol so produced as product.

14. A process according to claim 13 wherein the temperature is about 30° C. and pH about 6.

15. A process for the production of ethanol directly and simultaneously from D-glucose and D-xylose which comprises inoculating a medium comprising growth nutrients, D-glucose and D-xylose with a yeast mutant of the strain Candida sp. having an ability to ferment D-glucose and D-xylose to ethanol with a bioconversion yield of at least 80%, fermenting the innoculated medium for a period of time sufficient to achieve a conversion of D-xylose to ethanol of at least 80% and recovering the ethanol so produced as product.

16. A process according to claim 15 wherein the D-glucose and D-xylose are obtained from cellulose and hemicellulose hydrolyzate.

17. A process according to claim 1, 13 or 15 wherein said yeast mutant is obtained by purifying the parent yeast strain by single colony isolation, exposing the isolated single colony to irradiation to produce a mutated strain, and isolating a single colony of the mutated strain.

18. A process according to claim 13, 15 or 16 wherein said yeast mutant is Candida sp. XF 217.

* * * * *